US010682351B2

(12) United States Patent
Goss et al.

(10) Patent No.: US 10,682,351 B2
(45) Date of Patent: Jun. 16, 2020

(54) METHODS OF ADMINISTERING ELAGOLIX

(71) Applicant: AbbVie Inc., North Chicago, IL (US)

(72) Inventors: Sandra L. Goss, Wadsworth, IL (US); Cheri E. Klein, Northbrook, IL (US); Juki Wing-Keung Ng, Highland Park, IL (US); Ahmed Salem, Libertyville, IL (US)

(73) Assignee: ABBVIE INC., North Chicago, IL (US)

( * ) Notice: Subject to any disclaimer, the term of this patent is extended or adjusted under 35 U.S.C. 154(b) by 0 days.

(21) Appl. No.: 16/722,741

(22) Filed: Dec. 20, 2019

(65) Prior Publication Data

US 2020/0121680 A1 Apr. 23, 2020

Related U.S. Application Data

(63) Continuation of application No. 15/957,469, filed on Apr. 19, 2018, now Pat. No. 10,537,572, which is a continuation of application No. 15/254,419, filed on Sep. 1, 2016, now Pat. No. 9,949,974.

(60) Provisional application No. 62/213,000, filed on Sep. 1, 2015.

(51) Int. Cl.
| | | |
|---|---|---|
| *A61K 31/505* | (2006.01) | |
| *A61K 31/513* | (2006.01) | |
| *A61K 31/4178* | (2006.01) | |
| *A61K 31/496* | (2006.01) | |
| *A61K 31/567* | (2006.01) | |
| *A61K 31/565* | (2006.01) | |
| *A61K 9/00* | (2006.01) | |

(52) U.S. Cl.
CPC .......... *A61K 31/505* (2013.01); *A61K 9/0053* (2013.01); *A61K 31/4178* (2013.01); *A61K 31/496* (2013.01); *A61K 31/513* (2013.01); *A61K 31/565* (2013.01); *A61K 31/567* (2013.01)

(58) Field of Classification Search
None
See application file for complete search history.

(56) References Cited

FOREIGN PATENT DOCUMENTS

| WO | WO-2014143669 A1 | 9/2014 |
| WO | WO-2017040841 A1 | 3/2017 |

OTHER PUBLICATIONS

Bjorkhem-Bergman L., et al., "Quinine Compared to 4[beta]-Hydroxycholesterol and Midazolam as Markers for CYP3A Induction by Rifampicin,", Drug Metab. Pharmacokinet, 2014, vol. 29 (4), pp. 352-355.
Chen C., et al., "Discovery of Sodium R-(+)-4-{2-[5-(2-Fluoro-3-methoxyphenyl)-3-{2-fluoro-6-[trifluoromethyl]benzyl)-4-methyl-2,6-dioxo-3,6-dihydro-2Hpyrimidin-1-yl]-1-phenylethylamino}butyrat e (Elagolix), a Potent and Orally Available Nonpeptide Antagonist of the Human Gonadotropin-Releasing Hormone Receptor," Journal of Medicinal Chemistry, American Chemical Society, US, 2008, vol. 51 (23), pp. 7478-7485.
Diamond M.P., et al., "Elagolix Treatment for Endometriosis-Associated Pain: results from a Phase 2, Randomized , Double-Blind, Placebo-Controlled Study", Reproductive Sciences, Sage Publications, Inc, US, 2014, Vol . 21 (3), pp. 363-371.
Ezzati M., et al., "Elagoli x, a Novel, Orally bioavailable GnRH Antagonist Under Investigation for the Treatment of Endometriosis-Related Pain, " Women's Health, Future Medicine, UK, 2015, vol. 11 (1), pp. 19-28.
Imani R., et al., "Petal Study: Safety, Tolerability and Effectiveness of Elagolix, an Oral GnRH Antagonist for Endometriosis," Fertility and Sterility, Elsevier Science Inc, New York, NY, USA, 2009, vol. 92 (3), pp. S111-S112.
International Search Report and Written Opinion for Application No. PCT/US2016/049979, dated Dec. 7, 2016, 15 pages.
Kalliokoski A., et al., "Impact of OATP Transporters on Pharmacokinetics," British Journal of Pharmacology, 2009, vol. 158 (3), pp. 693-705.
Ng J., et al., "Effects of the Coadministration of Single and Multiple Doses of Rifampin on the Pharmacokinetics and Safety of Elagolix in Healthy Premenopausal Females," Clinical Pharmacology & Therapeutics, 2016, vol. 99 (1), pp. S54-S55.

*Primary Examiner* — Heidi Reese
(74) *Attorney, Agent, or Firm* — Neal, Gerber & Eisenberg LLP

(57) ABSTRACT

The present disclosure relates to the use of GnRH receptor antagonists used in the treatment of endometriosis or uterine fibroids. In particular, the present disclosure describes a method of treating endometriosis or uterine fibroids, where the method involves the administration of elagolix, and where the method may further involve the co-administration of rifampin or ketoconazole.

1 Claim, 2 Drawing Sheets

METHODS OF ADMINISTERING ELAGOLIX

CROSS-REFERENCE TO RELATED APPLICATIONS

This application is a continuation of U.S. patent application Ser. No. 15/957,469, filed Apr. 19, 2018, which is a continuation of U.S. patent application Ser. No. 15/254,419, filed Sep. 1, 2016, now U.S. Pat. No. 9,949,974, which claims priority to U.S. Provisional Application No. 62/213,000, filed Sep. 1, 2015. The contents of each of the aforementioned applications is incorporated herein by reference in its entirety.

FIELD

The present disclosure pertains to the use of GnRH receptor antagonists used in the treatment of endometriosis or uterine fibroids.

BACKGROUND 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid sodium salt ("Elagolix") is a drug currently in development of the treatment of the signs and symptoms of endometriosis and uterine fibroids.

Rifampin is an antibiotic used to treat bacterial infections. It is a potent CYP3A inducer and OATP inhibitor, and can typically lead to decreased exposure levels of many other drugs that are CYP enzyme substrates when co-administered.

Ketoconazole is a synthetic imidazole drug that may be used, for example, to treat fungal infections. It is a potent CYP3A and P-gp inhibitor.

SUMMARY

In embodiments, the present disclosure provides a method of treating endometriosis, where the method involves the administration of elagolix at a dose of 150 mg once per day ("q.d."), and further involves the co-administration of rifampin, after which the patient is treated at a dose of less than 150 mg elagolix once per day.

In embodiments, the present disclosure provides a method of treating endometriosis, where the method involves the administration of 150 mg of elagolix once per day, and further involves the co-administration of rifampin, after which the patient is treated with elagolix at a reduced dosing interval frequency of less than once per day.

In embodiments, the present disclosure provides a method of treating endometriosis, where the method comprises administering 200 mg elagolix twice daily ("b.i.d.") and further comprises the co-administration of rifampin, after which the patient is treated with elagolix b.i.d. at a dose of less than 200 mg.

In embodiments, the present disclosure provides a method of treating endometriosis, where the method involves the administration of 200 mg elagolix b.i.d. and further involves the co-administration of rifampin after which the patient is treated with elagolix at a reduced dosing interval frequency of less than twice per day.

In embodiments, the present disclosure provides a method of treating an endometriosis patient, where the method involves the b.i.d. administration of less than 200 mg elagolix and further comprises the co-administration of rifampin.

In embodiments, the present disclosure provides a method of treating an endometriosis patient, where the method involves the once daily administration of less than 150 mg elagolix and further comprises the co-administration of rifampin.

In embodiments, the present disclosure provides a method of treating a patient for uterine fibroids, where the method involves the administration of elagolix at 300 mg b.i.d. and further involves the co-administration of rifampin, after which the patient is treated with a reduced dosing interval of less than twice per day.

In embodiments, the present disclosure provides a method of treating an endometriosis patient, where the method involves the once daily administration of less than 150 mg elagolix and further involves the co-administration of rifampin.

In embodiments, the present disclosure provides a method for treating a patient for uterine fibroids, where the method involves the administration of elagolix at 300 mg b.i.d. and further involves the co-administration of rifampin, after which the patient is treated with a reduced dosing interval of less than twice per day.

In embodiments, the present disclosure provides a method of treating an endometriosis patient, where the method involves the administration of elagolix according to a first dosing schedule. In embodiments, the patient subsequently begins to take rifampin according to a rifampin dosing schedule, and the patient adjust the first dosing schedule of elagolix by reducing the amount of elagolix and/or by increasing the interval between doses according to a second dosing schedule. In embodiments, the second dosing schedule results in overall reduced elagolix exposure in the second dosing schedule relative to elagolix exposure in the first dosing schedule for a given time interval.

In embodiments, the present disclosure provides a method of treating a patient having uterine fibroids, where the method involves the administration of elagolix according to a first dosing schedule. In embodiments, the patent subsequently begins to take rifampin according to a rifampin dosing schedule, and the first dosing schedule of elagolix is adjusted by reducing the amount of elagolix and/or by increasing the interval between doses according to a second dosing schedule. In embodiments, the second dosing schedule results in in overall reduced elagolix exposure in the second dosing schedule relative to elagolix exposure in the first dosing schedule for a given time interval.

In embodiments, the present disclosure provides a method of treating endometriosis, where the method involves the administration of elagolix at a dose of 150 mg once per day ("q.d."), and further involves the co-administration of ketoconazole, after which the patient is treated at a dose of less than 150 mg elagolix once per day.

In embodiments, the present disclosure provides a method of treating endometriosis, where the method involves the administration of 150 mg of elagolix once per day, and further involves the co-administration of ketoconazole, after which the patient is treated with elagolix at a reduced dosing interval frequency of less than once per day.

In embodiments, the present disclosure provides a method of treating endometriosis, where the method comprises administering 200 mg elagolix twice daily ("b.i.d.") and further comprises the co-administration of ketoconazole, after which the patient is treated with elagolix b.i.d. at a dose of less than 200 mg.

In embodiments, the present disclosure provides a method of treating endometriosis, where the method involves the administration of 200 mg elagolix b.i.d. and further involves the co-administration of ketoconazole after which the patient is treated with elagolix at a reduced dosing interval frequency of less than twice per day.

In embodiments, the present disclosure provides a method of treating an endometriosis patient, where the method involves the b.i.d. administration of less than 200 mg elagolix and further comprises the co-administration of ketoconazole.

In embodiments, the present disclosure provides a method of treating an endometriosis patient, where the method involves the once daily administration of less than 150 mg elagolix and further comprises the co-administration of ketoconazole.

In embodiments, the present disclosure provides a method of treating a patient for uterine fibroids, where the method involves the administration of elagolix at 300 mg b.i.d. and further involves the co-administration of ketoconazole, after which the patient is treated with a reduced dosing interval of less than twice per day.

In embodiments, the present disclosure provides a method of treating an endometriosis patient, where the method involves the once daily administration of less than 150 mg elagolix and further involves the co-administration of ketoconazole.

In embodiments, the present disclosure provides a method for treating a patient for uterine fibroids, where the method involves the administration of elagolix at 300 mg b.i.d. and further involves the co-administration of ketoconazole, after which the patient is treated with a reduced dosing interval of less than twice per day.

In embodiments, the present disclosure provides a method of treating an endometriosis patient, where the method involves the administration of elagolix according to a first dosing schedule. In embodiments, the patient subsequently begins to take ketoconazole according to a ketoconazole dosing schedule, and the patient adjust the first dosing schedule of elagolix by reducing the amount of elagolix and/or by increasing the interval between doses according to a second dosing schedule. In embodiments, the second dosing schedule results in overall reduced elagolix exposure in the second dosing schedule relative to elagolix exposure in the first dosing schedule for a given time interval.

In embodiments, the present disclosure provides a method of treating a patient having uterine fibroids, where the method involves the administration of elagolix according to a first dosing schedule. In embodiments, the patent subsequently begins to take ketoconazole according to a ketoconazole dosing schedule, and the first dosing schedule of elagolix is adjusted by reducing the amount of elagolix and/or by increasing the interval between doses according to a second dosing schedule. In embodiments, the second dosing schedule results in in overall reduced elagolix exposure in the second dosing schedule relative to elagolix exposure in the first dosing schedule for a given time interval.

DETAILED DESCRIPTION

Figure 1:
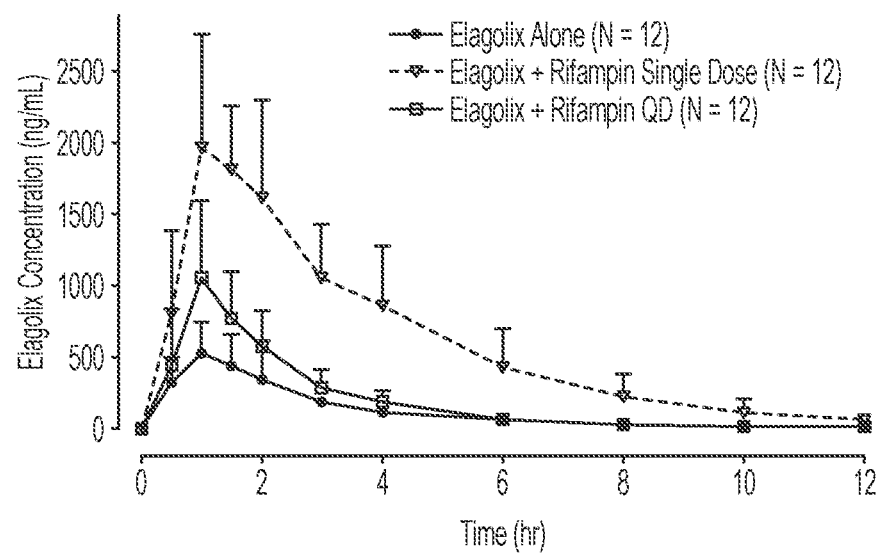
FIG. 1 shows Mean+SD Elagolix plasma concentration-time profiles for elagolix administered with single and multiple doses of rifampin, versus elagolix administered alone.

Elagolix is a small molecule antagonist of the GNRH receptor and its administration results in decreased levels of luteinizing hormone ("LH") and follicle stimulating hormone ("FSH") with corresponding suppression of the primary sex steroid hormones. Elagolix has shown significant effects in ameliorating many of the symptoms of endometriosis and uterine fibroids. The drug is currently being evaluated at 150 mg q.d. and 200 mg b.i.d. for endometriosis and 300 mg b.i.d. for fibroids.

During the course of drug-drug interaction studies, surprisingly it was discovered that rifampin significantly increased elagolix concentrations both acutely (after a single dose) and chronically after several doses. This discovery allows the possibility of reducing normal elagolix doses without compromising efficacy. In particular, it has been discovered that rifampin significantly increases elagolix exposures when the drugs are co-administered (present in the body at the same time). This result is surprising since rifampin is a known Cyp enzyme up-regulator and typically can lead to decreased exposure levels of many other drugs when co-administered. This discovery has the potential to modify accepted dosage regimens by decreasing the daily dosage and/or increasing the dosing interval (i.e., increasing the time between dosages). It has also been found that ketoconazole has the effect of increasing drug exposure levels and co-administration of elagolix with ketoconazole can also allow for a drug down-titration vis-à-vis dose or dosing interval adjustments.

In some embodiments of this invention, a revised elagolix dosing scheme is described wherein the dose of elagolix is down-titrated when administered with rifampin from the typical elagolix dose which is 150 mg q.d. or 200 mg b.i.d. for endometriosis. For example, the 150 mg dose could be reduced to 125 mg, 100 mg, 75 mg, 50 mg or integer multiples between. In embodiments, a revised elagolix dosing scheme is provided where the time between doses is increased, including for example, the possibility of going from a q.d. elagolix schedule to an every other day schedule or from a b.i.d. schedule to a q.d. schedule.

In embodiments, a revised elagolix dosing scheme is described wherein the dose of elagolix is down-titrated when co-administered with rifampin from the typical dose which is 300 mg b.i.d. for uterine fibroids. For example, the 300 mg dose could be reduced to 250 mg, 200 mg, 150 mg, 100 mg or integer multiples between. In embodiments, a revised elagolix dosing scheme is provided where the dosing interval is increased between dosing, including for example, the possibility of going from a b.i.d. schedule to a q.d. schedule.

In the broader sense, it is important to consider that the dosing schedules that are adjusted can be done for a period of time but do not have to stay fixed at their adjusted level. Nor do they need to be reduced to a fixed schedule. Many of those specifically enumerated herein which are provided for by way of just some examples. The physician or patient has the option of reducing to any lower dose and/or increasing the period between doses for as long as needed, after which time they can adjust to a new reduced dose schedule or revert back to their original dose schedule. This provides maximum flexibility for the patient and/or physician to titrate the drug to his or her individual need and at their discretion.

In embodiments, the dosage regimen may modified by decreasing the daily dosage. For example, in embodiments, the present disclosure provides a method of treating endometriosis, where the method involves the administration of elagolix at a dose of 150 mg once per day. In embodiments, the method further involves the co-administration of rifampin, after which the patient is treated at a dose of less than 150 mg elagolix once per day.

In embodiments, the present disclosure provides a method of treating endometriosis, where the method involves the administration of 200 mg elagolix twice daily (b.i.d.). In embodiments, the method further involves the co-administration of rifampin, after which the patient is treated with elagolix b.i.d. at a dose of less than 200 mg.

In embodiments, the dosage regimen may be modified by increasing the dosing interval (i.e., increasing the time between dosages). For example, in embodiments, the present disclosure provides a method of treating endometriosis, where the method involves the administration of 150 mg elagolix once per day. In embodiments, the method further comprises the co-administration of rifampin, after which the patient is treated with elagolix at a reduced dosing interval frequency of less than once per day. In embodiments, the reduced dosing interval frequency may be once per every other day.

In embodiments, the present disclosure provides a method of treating endometriosis, where the method involves the administration of 20 mg elagolix b.i.d. In embodiments, the method further comprises the co-administration of rifampin, after which the patient is treated with elagolix at a reduced dosing interval frequency of less than twice per day. For example, in embodiments, the reduced dosing interval is once per day. In embodiments, the method further involves the administration of an estrogen and a progestin. In embodiments, the estrogen is 17β-estradiol and said progestin is norethindrone acetate.

In embodiments, the present disclosure provides a method of treating an endometriosis patient, where the method involves the b.i.d. administration of less than 200 mg elagolix and further comprises the co-administration of rifampin.

In embodiments, the present disclosure provides a method of treating an endometriosis patient, where the method involves the once daily administration of less than 150 mg elagolix, and further involves the co-administration of rifampin.

In embodiments, the present disclosure provides a method of treating uterine fibroids, where the method involves the administration of elagolix at 300 mg b.i.d. and further comprises the co-administration of rifampin, after which the patient is treated with a reduced dosing interval of less than twice per day. In embodiments, the reduced dosing interval is once per day. In embodiments, the patient is further treated with an estrogen and a progestin. In embodiments, the estrogen is 17β-estradiol and said progestin is norethindrone acetate.

In embodiments, the administration is per the oral route.

In embodiments, in the methods described in the present disclosure, rifampin is given as 600 mg twice per day. In embodiments, in the methods described in the present disclosure, rifampin is given at a dose of about 10 mg/kg per day.

In embodiments, the present disclosure provides a method of treating endometriosis, where the method involves the administration of elagolix according to a first dosing schedule. The patient subsequently begins to take rifampin according to a rifampin dosing schedule. After the patient begins to take rifampin according to the rifampin dosing schedule, the first dosing schedule of elagolix is adjusted. In embodiments, the first dosing schedule is reduced by reducing the amount of elagolix and/or by increasing the interval between doses according to a second dosing schedule. In embodiments, the second dosing schedule results in overall reduced elagolix exposure in the second dosing schedule relative to elagolix exposure in the first dosing schedule for a given time interval.

In embodiments, in the first dosing schedule, elagolix is administered at 150 mg once per day, and in the second dosing schedule, elagolix is administered at less than 150 mg per day, and/or elagolix is administered once every other day or less.

In embodiments, the first dosing schedule involves administering elagolix at 200 mg b.i.d., and the second dosing schedule involves the administration of less than 200 mg per dose and/or dosing less than twice per day. For example, in the second dosing schedule, with respect to dosing less than twice per day, in embodiments elagolix is administered once per day.

In embodiments, the present disclosure provides a method of treating a patient having uterine fibroids, where the method involves the administration of elagolix according to a first dosing schedule. In embodiments, the patient subsequently begins to take rifampin according to a rifampin dosing schedule, and the first dosing schedule of elagolix is adjusted by reducing the amount of elagolix per dose and/or by increasing the interval between doses according to a second dosing schedule. In embodiments, the second dosing schedule results in overall reduced elagolix exposure in the second dosing schedule relative to elagolix exposure in the first dosing schedule for a given time period. In embodiments, according to the first dosing schedule, elagolix is administered at 300 m.g. b.i.d., and according to the second dosing schedule, elagolix is administered at less than 300 mg per dose, and/or elagolix is administered less than twice per day. For example, with respect to administering elagolix less than twice per day in the second dosing schedule, in embodiments, elagolix is administered once per day. In embodiments, the method further comprises administering an estrogen and a progestin. In embodiments, the estrogen is 17β-estradiol and said progestin is noerthindrone acetate.

In embodiments, all of the drugs may be taken orally.

As discussed above, it was further determined that ketoconazole has the effect of increasing drug exposure levels. Accordingly, co-administration of elagolix with ketoconazole can also allow for a drug down-titration with respect to dose or dosing interval adjustments.

In embodiments, a revised elagolix dosing scheme is described wherein the dose of elagolix is down-titrated when administered with ketoconazole from the typical elagolix dose which is 150 mg q.d. or 200 mg b.i.d. for endometriosis. For example, the 150 mg dose could be reduced to 125 mg, 100 mg, 75 mg, 50 mg or integer multiples between. In certain embodiments of this invention a revised elagolix dosing scheme is provided where the time between doses is increased, including for example, the possibility of going from a q.d. elagolix schedule to an every other day schedule or from a b.i.d. schedule to a q.d. schedule.

In some embodiments of this invention, a revised elagolix dosing scheme is described wherein the dose of elagolix is down-titrated when co-administered with ketoconazole from the typical dose which is 300 mg b.i.d. for uterine fibroids. For example, the 300 mg dose could be reduced to 250 mg, 200 mg, 150 mg, 100 mg or integer multiples between. In certain embodiments of this invention a revised elagolix dosing scheme is provided where the dosing interval is increased between dosing, including for example, the possibility of going from a b.i.d. schedule to a q.d. schedule.

In embodiments, the dosage regimen may be modified by decreasing the daily dosage. For example, in embodiments, the present disclosure provides a method of treating endometriosis, where the method involves the administration of elagolix at a dose of 150 mg once per day. In embodiments, the method further involves the co-administration of ketoconazole, after which the patient is treated at a dose of less than 150 mg elagolix once per day.

In embodiments, the present disclosure provides a method of treating endometriosis, where the method involves the administration of 200 mg elagolix twice daily (b.i.d.). In embodiments, the method further involves the co-administration of ketoconazole, after which the patient is treated with elagolix b.i.d. at a dose of less than 200 mg.

In embodiments, the dosage regimen may be modified by increasing the dosing interval (i.e., increasing the time between dosages). For example, in embodiments, the present disclosure provides a method of treating endometriosis, where the method involves the administration of 150 mg elagolix once per day. In embodiments, the method further comprises the co-administration of ketoconazole, after which the patient is treated with elagolix at a reduced dosing interval frequency of less than once per day. In embodiments, the reduced dosing interval frequency may be once per every other day.

In embodiments, the present disclosure provides a method of treating endometriosis, where the method involves the administration of 20 mg elagolix b.i.d. In embodiments, the method further comprises the co-administration of ketoconazole, after which the patient is treated with elagolix at a reduced dosing interval frequency of less than twice per day. For example, in embodiments, the reduced dosing interval is once per day. In embodiments, the method further involves the administration of an estrogen and a progestin. In embodiments, the estrogen is 17β-estradiol and said progestin is norethindrone acetate.

In embodiments, the present disclosure provides a method of treating an endometriosis patient, where the method involves the b.i.d. administration of less than 200 mg elagolix and further comprises the co-administration of ketoconazole.

In embodiments, the present disclosure provides a method of treating an endometriosis patient, where the method involves the once daily administration of less than 150 mg elagolix, and further involves the co-administration of ketoconazole.

In embodiments, the present disclosure provides a method of treating uterine fibroids, where the method involves the administration of elagolix at 300 mg b.i.d. and further comprises the co-administration of ketoconazole, after which the patient is treated with a reduced dosing interval of less than twice per day. In embodiments, the reduced dosing interval is once per day. In embodiments, the patient is further treated with an estrogen and a progestin. In embodiments, the estrogen is 17β-estradiol and said progestin is norethindrone acetate.

In embodiments, the administration is per the oral route.

In embodiments, the present disclosure provides a method of treating endometriosis, where the method involves the administration of elagolix according to a first dosing schedule. The patient subsequently begins to take ketoconazole according to a ketoconazole dosing schedule. After the patient begins to take ketoconazole according to the ketoconazole dosing schedule, the first dosing schedule of elagolix is adjusted. In embodiments, the first dosing schedule is reduced by reducing the amount of elagolix and/or by increasing the interval between doses according to a second dosing schedule. In embodiments, the second dosing schedule results in overall reduced elagolix exposure in the second dosing schedule relative to elagolix exposure in the first dosing schedule for a given time interval.

In embodiments, in the first dosing schedule, elagolix is administered at 150 mg once per day, and in the second dosing schedule, elagolix is administered at less than 150 mg per day, and/or elagolix is administered once every other day or less.

In embodiments, the first dosing schedule involves administering elagolix at 200 mg b.i.d., and the second dosing schedule involves the administration of less than 200 mg per dose and/or dosing less than twice per day. For example, in the second dosing schedule, with respect to dosing less than twice per day, in embodiments elagolix is administered once per day.

In embodiments, the present disclosure provides a method of treating a patient having uterine fibroids, where the method involves the administration of elagolix according to a first dosing schedule. In embodiments, the patient subsequently begins to take ketoconazole according to a ketoconazole dosing schedule, and the first dosing schedule of elagolix is adjusted by reducing the amount of elagolix per dose and/or by increasing the interval between doses according to a second dosing schedule. In embodiments, the second dosing schedule results in overall reduced elagolix exposure in the second dosing schedule relative to elagolix exposure in the first dosing schedule for a given time period. In embodiments, according to the first dosing schedule, elagolix is administered at 300 m.g. b.i.d., and according to the second dosing schedule, elagolix is administered at less than 300 mg per dose, and/or elagolix is administered less than twice per day. For example, with respect to administering elagolix less than twice per day in the second dosing schedule, in embodiments, elagolix is administered once per day. In embodiments, the method further comprises administering an estrogen and a progestin. In embodiments, the estrogen is 17β-estradiol and said progestin is noerthindrone acetate.

In embodiments, all of the drugs may be taken orally.

The term "co-administered" means, for instance, the drugs can be taken together or sequentially.

Certain aspects of the disclosure are described in greater detail in the non-limiting Examples that follow:

Example 1

This study was designed to assess the pharmacokinetic interaction between elagolix and rifampin (a potent CYP3A inducer and OATP inhibitor) and the safety in healthy premenopausal females. This was an open-label, two-period, sequential study conducted in 12 females chosen according to the protocol selection criteria. Each subject received elagolix 150 mg single dose with and without rifampin 600 mg q.d. for 10 days. Intensive blood samples for elagolix assay were collected up to 36 hours after elagolix dosing in both periods. Safety data, including adverse event monitoring, vital signs, ECGs, and laboratory tests were collected during the study.

Values for elagolix maximum concentration ($C_{max}$) and area-under-the-curve (AUC) were estimated using noncompartmental methods. Analysis of variance was performed to compare elagolix $C_{max}$ and AUC with and without rifampin. Elagolix $C_{max}$ and AUC increased by 4.4 and 5.6 fold, when co-administered with a single rifampin dose, and increased by 2.0 and 1.65 fold after multiple rifampin doses, respectively. Adverse event rates across treatment periods were 41.7% (elagolix alone), 83.3% (rifampin alone), and up to 50.0% (co-administration). The most common adverse events were GI-related, occurring most frequently with rifampin alone. No clinically significant vital signs, ECG or laboratory measurements were observed during the study. Inhibition of OATP by rifampin increases elagolix concentrations even after accounting for rifampin's inductive effects after multiple dosing. There were no new or unknown safety findings in this study. Mean and SD Elagolix plasma concentration-time profiles for elagolix administered with single and multiple doses of rifampin, versus elagolix administered alone, are shown in FIG. 1.

Example 2

In a second embodiment of this invention, it was discovered that ketoconazole increased elagolix exposure levels. This study was designed to assess the pharmacokinetic interaction between elagolix and ketoconazole (a potent CYP3A and P-gp inhibitor) and the safety in healthy pre-menopausal females.

This was an open-label, two-period, sequential study conducted in 12 healthy premenopausal females chosen according to the protocol selection criteria. Each subject received elagolix 150 mg single dose alone and on the 4$^{th}$ day of a six-day regimen of ketoconazole 400 mg q.d.

Intensive blood samples for elagolix assay were collected up to 72 hours after elagolix dosing in both periods. Safety data, including adverse event monitoring, vital signs, ECGs, and laboratory tests were collected during the study.

Values for elagolix maximum concentrations ($C_{max}$) and area-under-the-curve (AUC) were estimated using noncompartmental methods. Analysis of variance was performed to compare the pharmacokinetic parameters of elagolix with and without ketoconazole.

Figure 2:
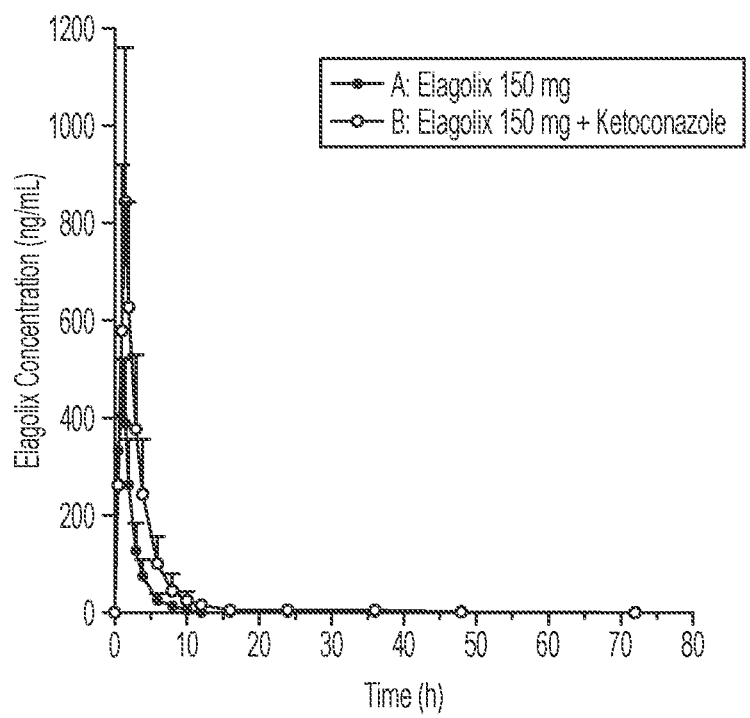
FIG. 2 shows mean elagolix plasma concentration—time profiles for elagolix administered with ketoconazole, versus elagolix administered alone.

When coadministered with ketoconazole, elagolix $C_{max}$ and AUC values increased 1.8- and 2.2-fold, respectively, relative to administration of elagolix alone. Adverse event rates across treatment periods were 0% (elagolix alone), 82% (ketoconazole alone), and 36% (co-administration). The most common adverse event was nausea, which was noted as probably related to ketoconazole alone. No clinically significant vital signs, ECG or laboratory measurements were observed during the study. Mean elagolix plasma concentration—time profiles for elagolix administered with ketoconazole, versus elagolix administered alone, are shown in FIG. 2.

It is to be understood that the foregoing detailed description and accompanying examples are merely illustrative and are not to be taken as limitations upon the scope of the disclosure, which is defined by the appended claims and their examples.

The invention claimed is:

1. A method for treating endometriosis in a patient, the method comprising:
orally administering to the patient once daily 4-((R)-2-[5-(2-fluoro-3-methoxy-phenyl)-3-(2-fluoro-6-trifluoromethyl-benzyl)-4-methyl-2,6-dioxo-3,6-dihydro-2H-pyrimidin-1-yl]-1-phenyl-ethylamino)-butyric acid as a sodium salt (elagolix), wherein the sodium salt is administered in an amount equivalent to 150 mg of the free acid;
wherein the patient receives a once daily dose of 400 mg of ketoconazole, wherein maximum plasma concentration for elagolix is increased by 1.8 fold relative to administration of elagolix alone and wherein plasma area-under-the-curve for elagolix is increased by 2.2 fold relative to administration of elagolix alone.

* * * * *